United States Patent [19]

Vértesy et al.

[11] Patent Number: 6,022,851
[45] Date of Patent: Feb. 8, 2000

[54] LANTIBIOTIC RELATED TO ACTAGARDINE, AND PROCESSES FOR THE PREPARATION AND USE THEREOF

[75] Inventors: Laszló Vértesy, Eppstein; Herbert Kogler, Glashütten; Matthias Schiell, Brechen; Joachim Wink, Rödermark, all of Germany

[73] Assignee: Hoechst Marion Roussel Deutschland, GmbH, Frankfurt am Main, Germany

[21] Appl. No.: 09/172,042

[22] Filed: Oct. 14, 1998

[30] Foreign Application Priority Data

Oct. 15, 1997 [DE] Germany ............................ 197 45 583

[51] Int. Cl.⁷ .......................... A61K 38/04; A61K 38/12; C07K 1/107; C07K 4/04
[52] U.S. Cl. ...................... 514/9; 514/2; 514/13; 435/71.3; 435/71.1; 530/317; 530/326; 530/333
[58] Field of Search .................. 435/71.3, 71.1; 514/2, 9, 13; 530/333, 317, 326

[56] References Cited

U.S. PATENT DOCUMENTS 4,022,884  5/1977  Parenti et al. ........................... 424/117
4,684,644  8/1987  Malabarba et al. ...................... 514/210

OTHER PUBLICATIONS

Jung, Lantibiotics–Ribosomally Synthesized Biologically Active Polypeptides containing Sulfide Bridges and α,β–Didehydroamino Acids, Chem. Int. Ed. Engl., vol. 30:1051–1068 (1991).

Zimmermann et al., The tetracyclic lantibiotic actagardine $^1$H–NMR and $^{13}$C–NMR assignments and revised primary structure, Eur. J. Biochem., vol. 228:786–797 (1995).

Somma et al., Gardimycin, a New Antibiotic Inhibiting Peptidoglycan Synthesis, Antimicrobial Agents and Chemotherapy, vol. 11(3):396–401 (1977).

Malabarba et al., Physico–Chemical and Biological Properties of Actagardine and Some Acid Hydrolysis Products, The Journal of Antibiotics, vol. 38(11):1506–1511 (1985).

*Primary Examiner*—Michael P. Woodward
*Assistant Examiner*—Michael Borin
*Attorney, Agent, or Firm*—Finnegan, Henderson, Farabow, Garrett & Dunner, L.L.P.

[57] ABSTRACT

The present invention relates to a novel lantibiotic having the formula $NH_2$—R-actagardine, where $NH_2$—R is the radical of the amino acid alanine, which is formed by the microorganism *Actinoplanes liguriae*, DSM 11797 or *Actinoplanes garbadiensis*, DSM 11796 during fermentation, chemical derivatives of the lantibiotic, a process for its preparation and the use of the lantibiotics as pharmaceuticals.

13 Claims, No Drawings

SEQUENCE LISTING

<160> NUMBER OF SEQ ID NOS: 1

<210> SEQ ID NO 1
<211> LENGTH: 20
<212> TYPE: PRT
<213> ORGANISM: Actinoplanes liguriae and/or garbadiensis
<220> FEATURE:
<223> OTHER INFORMATION: Xaa at position 1 is the radical of a natural
      amino acid, preferably Ala.
<220> FEATURE:
<221> NAME/KEY: MOD_RES
<222> LOCATION: (8)
<223> OTHER INFORMATION: Abu
<220> FEATURE:
<221> NAME/KEY: MOD_RES
<222> LOCATION: (10)
<223> OTHER INFORMATION: Abu
<220> FEATURE:
<221> NAME/KEY: MOD_RES
<222> LOCATION: (15)
<223> OTHER INFORMATION: Abu

<400> SEQUENCE: 1

Xaa Ala Ser Gly Trp Val Ala Xaa Leu Xaa Ile Glu Ala Gly Xaa Val
 1               5                  10                  15

Ile Ala Ala Ala
            20

LANTIBIOTIC RELATED TO ACTAGARDINE, AND PROCESSES FOR THE PREPARATION AND USE THEREOF

The present invention relates to a novel lantibiotic related to actagardine, particularly a lantibiotic having the designation Ala$^0$-actagardine, a process for its preparation, chemical derivatives derived from the lantibiotic and the use of the antibiotics as pharmaceuticals.

A relatively large number of antibiotics have already been described. Lantibiotics are polycyclic peptide antibiotics which as a characteristic feature contain the amino acid lanthionine or methyllanthionine. They are natural substances obtained microbially, which are used as antibacterial active compounds in human therapy, as preservatives or as enzyme inhibitors (G. Jung, Angew. Chem. Int. Ed. Engl., 1991, 30, 1051–1068).

A large number of antibiotics are employed therapeutically for the treatment of bacterial infectious diseases. The pathogens, however, are becoming increasingly resistant to the pharmaceuticals used, a great danger even threatens due to so-called multiresistant microorganisms, which have become resistant not only to individual antibiotic groups, such as, for example, β-lactam antibiotics or glycopeptides or macrolides, but at the same time carry several resistances. There are even pathogens which have become resistant to all commercially available antibiotics. Infectious diseases which are caused by these microorganisms can no longer be treated. There is therefore a great need for novel agents which can be employed against resistant microorganisms. Although many thousands of antibiotics have been described in the literature, most, however, are too toxic to be able to be employed as pharmaceuticals.

Actagardine is a lantibiotic which S. Somma et al. described for the first time in Antimicrob. Agents Chemother. 11, 396–401 in 1977. Its structure was only recently correctly elucidated (N. Zimmermann et al., Eur. J. Biochem. 1995, 228, 786–797).

It has surprisingly been found that the strains *Actinoplanes liguriae* and *Actinoplanes garbadiensis* in each case are able to form at least one novel antibiotic, e.g. Ala$^0$-actagardine, which is not only antibacterially very active, but also highly tolerable. An isolate of *Actinoplanes liguriae* was deposited in the Deutsche Sammlung von Mikroorganismen und Zellkulturen GmbH [German Collection of Microorganisms and Cell Cultures GmbH], Mascheroder Weg 1B, 38124 Braunschweig, Germany (hereafter 'DSM'), according to the rules of the Budapest Convention on Sep. 24, 1997 under the following number: DSM 11797. An isolate of *Actinoplanes garbadiensis* was deposited in the DSM according to the rules of the Budapest Convention on Sep. 24, 1997 under the following number: DSM 11796.

Correspondingly, the invention presents compounds of the formula I

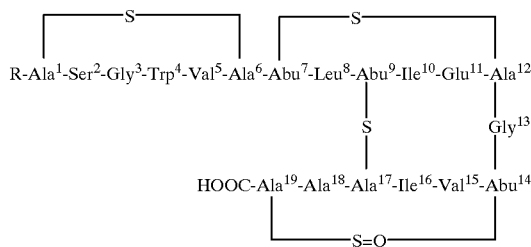

where R is the radical of an amino acid, and their physiologically tolerable salts. R can be the radical of a substituted or unsubstituted amino acid in which the amino group is in the α- to ω-position and in the D or L configuration. Substituted or unsubstituted α-amino acids in the D or L configuration are particularly preferred.

Preferably, R is the radical of a natural amino acid selected from the group consisting of: Ala, Gly, Glu, Phe, Pro, Thr, Cys, Met, Trp, Tyr, Asn, Gln, Asp, His, Ile, Leu, Lys, Arg, Ser and Val. The amino acid is particularly preferably Ala, Ile, Lys, Phe, Val, Glu, Asp, His, Leu, Arg or Ser and very particularly preferably the amino acid is Ala$^0$.

R can also be a substituted or unsubstituted diaminoalkanoic acid radical such as, for example, 2,4-diaminobutyric acid (Dab).

The invention additionally relates to a compound of the empirical formula: $C_{84}H_{129}N_{21}O_{25}S_4$ (Ala$^0$-actagardine) obtainable by fermentation of *Actinoplanes liguriae*, DSM 11797 or *Actinoplanes garbadiensis*, DSM 11796 or of one of their variants and/or mutants, in a culture medium until the compound Ala$^0$-actagardine accumulates in the culture broth and by subsequent isolation of the compound, and its pharmacologically tolerable salts.

The invention furthermore relates to chemical derivatives derived from a compound of the empirical formula $C_{84}H_{129}N_{21}O_{25}S_4$ (Ala$^0$-actagardine), obtainable by fermentation of *Actinoplanes liguriae*, DSM 11797 or *Actinoplanes garbadiensis*, DSM 11796 or of one of their variants and/or mutants in a culture medium until the compound Ala$^0$-actagardine accumulates in the culture broth and by subsequent isolation of the compound and conversion into chemical derivatives, and its pharmacologically tolerable salts.

Preferred chemical derivatives are: Ile$^0$-, Lys$^0$-, Phe$^0$-, Val$^0$-, Glu$^0$-, Asp$^0$-, His$^0$-, Leu$^0$-, Arg$^0$- and Ser$^0$-actagardine. The conversion of Ala$^0$-actagardine into the chemical derivatives mentioned can be carried out by methods known to the person skilled in the art.

The antibiotic Ala$^0$-actagardine differs from substances known from the literature by means of the structural formulae indicated. Beside actagardine, some actagardine secondary components have additionally been described (U.S. Pat. No. 4,022,884 of May 10, 1976 and A. Malabarba et al., J. Antibiotics, 1985, 38, 1506–1511), which, however, all differ either by means of the polarity, also with respect to actagardine, or by means of the amino acid composition or by means of the antimicrobial activity or by means of further physical properties of the compounds according to the invention.

The strain *Actinoplanes liguriae*, DSM 11797 forms actagardine and the by-products known from the literature on glucose-, starch- or glycerol-containing nutrient solutions. It has surprisingly been found that the same organism produces the antibiotic NH$_2$—R-actagardine according to the invention on poorly digestible, mannitol-containing media in very good yields, where R is the radical of a natural amino acid, particularly alanine, but does not produce the known compounds described, actagardine itself being produced only in traces.

The invention therefore furthermore relates to a process for the preparation of the compound of the formula I, which comprises culturing the microorganism *Actinoplanes liguriae*, DSM 11797 or *Actinoplanes garbadiensis*, DSM 11796 or one of their variants or mutants in an aqueous nutrient medium, isolating and purifying a compound of the formula I and, if appropriate, converting it into its pharmacologically tolerable salts.

Said process comprises the culturing of *Actinoplanes liguriae*, DSM 11797 or *Actinoplanes garbadiensis*, DSM 11796, of its mutants and/or variants under aerobic conditions in culture media containing a carbon and nitrogen source, inorganic salts and trace elements.

Culturing is preferably carried out at a temperature between 20 and 35° C. and at a pH between 4 and 10.

The invention additionally relates to a process for the preparation of a compound of the formula I, which comprises reacting the compound actagardine with an amino acid.

For example, an activated amino acid ester can be reacted with the terminal amino group of the actagardine. A protective group, such as, for example, tert-butyloxycarbonyl (Boc-), is preferably bonded to the amino nitrogen of the amino acid in order to prevent reactions of the activated amino acid esters with themselves. Activated esters are, for example, the N-hydroxysuccinimide ester of the respective amino acids. The protective group is removed and the reaction mixture is then purified.

Actinoplanes has orange substrate mycelium and no aerial mycelium. It forms the sporangia characteristic of Actinoplanes. The cell wall contains mesodiaminopimelic acid and glycine as characteristic amino acids and xylose and arabinose as sugars; these are characteristic features of the genus Actinoplanes.

Instead of the strain DSM 11797 or 11796, its mutants and variants can also be employed if they synthesize the compounds according to the invention. Such mutants can be produced in a known manner by physical means, for example irradiation, such as with ultraviolet or X-rays, or chemical mutagens, such as, for example, ethyl methanesulfonate (EMS); 2-hydroxy-4-methoxybenzophenone (MOB) or N-methyl-N'-nitro-N-nitroso-guanidine (MNNG).

Screening for mutants and variants which produce the antibiotic according to the invention can be carried out by determination of the biological activity of the active compound accumulated in the culture broth, for example by testing the antibacterial action.

Preferred carbon sources suitable for aerobic fermentation are assimilable, but poorly digestible carbohydrates and sugar alcohols, such as mannitol, inositol and carbohydrate-containing natural products, such as, for example, soybean flour. Suitable nitrogen-containing nutrients are: amino acids, peptides and proteins and their degradation products, such as peptones or tryptones, furthermore meat extracts, ground seeds, for example of corn, wheat, beans, oats, soybeans or the cotton plant, distillation residues from alcohol production, meat meals or yeast extracts, but also ammonium salts and nitrates. Inorganic salts which the nutrient solution can contain are, for example, chlorides, carbonates, sulfates or phosphates of the alkali metals or alkaline earth metals, iron, zinc, cobalt and manganese.

The formation of the Ala(0)-actagardine proceeds particularly well, for example, in a nutrient solution which contains approximately 0.5 to 5% of mannitol, preferably 1 to 3%, 0.5 to 5% of soybean flour, preferably 1 to 3% and a trace element solution in a concentration of 0.1 to 0.5%, preferably 0.2 to 0.3%. The trace element solution contains $CaCl_2$, Fe(III) citrate, $MnSO_4$, $ZnCl_2$, $CuSO_4$, sodium tetraborate, $CoCl_2$ and sodium molybdate.

Culturing is carried out aerobically, i.e., for example submerse with shaking or stirring in shaker flasks or fermenters, if appropriate with introduction of air or oxygen. Fermentation can be carried out, for example, in wide-necked bottles or round-bottomed flasks of various volumes, in glass fermenters or $V_2A$ steel tanks. It can be carried out in a temperature range from approximately 20 to 35° C., preferably at approximately 25 to 30° C. The pH should be between 4 and 10, advantageously between 5.5 and 8.5. The microorganism is in general cultured under these conditions over a period of 20 to 300 hours, preferably 24 to 140 hours. Culturing is advantageously carried out in several stages, i.e. one or more precultures is first prepared in a liquid nutrient medium, which is then transferred to the actual production medium, the main culture, for example in the volume ratio 1:10. The preculture is obtained, for example, by transferring a mycelium into a nutrient solution and allowing it to grow for approximately 20 to 120 hours, preferably 24 to 72 hours. The mycelium can be obtained, for example, by allowing the strain to grow for approximately 1 to 40 days, preferably 3 to 10 days, on a solid or liquid nutrient medium, for example yeast-malt agar or oatmeal agar.

The course of the fermentation and the formation of the antibiotic according to the invention can be monitored according to methods known to the person skilled in the art, such as, for example, by testing the biological activity in bioassays or by chromatographic methods such as thin-layer chromatography (TLC) or high-performance liquid chromatography (HPLC).

The antibiotic Ala(0)-actagardine can occur both in the mycelium and in the culture filtrate, usually the main amount is in the culture filtrate. It is therefore expedient to separate the fermentation solution by filtration or centrifugation. The filtrate is extracted using an adsorption resin as a solid phase. The mycelium is expediently extracted with methanol or acetone; however, other solvents can also be used.

The extractions can be carried out in a wide pH range, however, it is expedient to work in neutral or weakly acidic medium, preferably between pH 3 and pH 7. The extracts can be concentrated and dried, e.g. in vacuo.

One method of isolation of the antibiotic according to the invention is solution partition in a manner known per se.

Another method of purification is chromatography on adsorption resins such as, for example, on Diaion® HP-20 (Mitsubishi Casei Corp., Tokyo), on Amberlite® XAD 7 (Rohm and Haas, USA), on Amberchrom® CG, (Toso Haas, Philadelphia, USA) or on similar resins. Numerous reverse-phase supports are moreover suitable, e.g. $RP_8$ and $RP_{18}$, such as have been generally publicized, for example, in the context of high-pressure liquid chromatography (HPLC).

A further possibility of purification of the antibiotic according to the invention consists in the use of so-called normal-phase chromatography supports, such as, for example, silica gel or $Al_2O_3$ or others in a manner known per se.

An alternative isolation process is the use of molecular sieves, such as, for example, Fractogel® TSK HW-40, Sephadex® G-25 and others, in a manner known per se. It is moreover also possible to obtain the Ala(0)-actagardine from enriched material by crystallization. For example, organic solvents and their mixtures, anhydrous or with addition of water, are suitable for this purpose. An additional process for the isolation and purification of the antibiotics according to the invention consists in the use of anion exchangers, preferably in the pH range from 4 to 10, and cation exchangers, preferably in the pH range from 2 to 5. The use of buffer solutions to which amounts of organic solvents have been added is particularly suitable for this purpose.

Ala(0)-actagardine, the mentioned chemical derivatives thereof and the obvious chemical equivalents thereof can be converted by methods known to the person skilled in the art into the corresponding pharmacologically tolerable salts.

Obvious chemical equivalents of the compounds according to the invention are compounds which have a slight chemical difference, i.e. have the same activity or are converted into the compounds according to the invention under mild conditions. The equivalents mentioned include, for example, esters, amino derivatives, complexes or adducts of the or with the compounds according to the invention.

Pharmacologically tolerable salts of the compounds according to the invention are understood as meaning both inorganic and organic salts, such as are described in Remington's Pharmaceutical Sciences (17th Edition, page 1418 (1985)). Possible salts are in particular alkali metal salts, ammonium salts, alkaline earth metal salts, salts with physiologically tolerable amines and salts with inorganic or organic acids such as, for example, HCl, HBr, $H_2SO_4$, maleic acid, fumaric acid.

The physicochemical and spectroscopic properties of the antibiotics according to the invention can be summarized as follows:

Ala(0)-actagardine:
Appearance:
Colorless substance soluble in methanol and water. Stable in neutral and mildly alkaline medium, but unstable in strongly acidic and strongly alkaline solution.
Empirical formula: $C_{84}H_{129}N_{21}O_{25}S_4$
Molecular weight: 1961.21
$^1$H- and $^{13}$C-NMR: see Table 1 and 1
UV maxima (log ε): 280 nm (3.71), 288 nm (shoulder)

TABLE 1

$^1$H-NMR spectroscopic data of Ala$^0$-actagardine

| Amino acid | HN | Hα | Hβ | Hγ | Other |
|---|---|---|---|---|---|
| Ala$^0$ | 8.010 | 2.891 | 1.383 | | |
| Ala$^1$ | 8.564 | 4.727 | 3.397 2.603 | — | |
| Ser$^2$ | 8.264 | 4.350 | 3.651 | | OH: 5.102 |
| Gly$^3$ | 8.595 | 3.968 3.263 | — | — | |
| Trp$^4$ | 8.147 | 4.475 | 3.311 | | H5: 7.144; H6: 7.554; H7: 6.983; H8: 7.061; H9: 7.333; indole: 10.740 |
| | | | 2.978 | | |
| Val$^5$ | 7.454 | 4.558 | 2.048 | 0.909 0.856 | |
| Ala$^6$ | 8.487 | 4.704 | 2.578 2.960 | | |
| Abu$^7$ | 8.324 | 4.557 | 3.596 | 1.176 | |
| Leu$^8$ | 7.636 | 4.626 | 1.418 1.482 | 1.482 γ-Me: 0.860 | δ0.841 |
| Abu$^9$ | 7.604 | 4.747 | 3.570 | 1.207 | |
| Ile$^{10}$ | 8.378 | 3.763 | 1.605 β-Me: 0.879 | 1.063 1.642 | δ-Me: 0.860 |
| Glu$^{11}$ | 8.262 | 3.690 | 2.178 | 2.319 | |
| Ala$^{12}$ | 7.325 | 4.553 | 2.559 2.866 | — | |
| Gly$^{13}$ | 8.140 | 3.538 4.167 | — | — | |
| Abu$^{14}$ | 7.860 | 4.381 | 3.336 | 1.059 | |
| Val$^{15}$ | 7.778 | 4.104 | 2.042 | 0.875 0.873 | |
| Ile$^{16}$ | 7.589 | 3.867 | 1.875 β-Me: 0.889 | 1.513 1.115 | δ-Me: 0.833 |
| Ala$^{17}$ | 7.577 | 4.488 | 2.594 2.878 | | |
| Ala$^{18}$ | 8.181 | 4.036 | 1.232 | | |
| Ala$^{19}$ | 8.342 | 4.447 | 2.934 3.069 | | |

TABLE 2

$^{13}$C-NMR spectroscopic data of Ala$^0$-actagardine

| Amino acid | CO | Cα | Cβ | Cγ | Other |
|---|---|---|---|---|---|
| Ala$^0$ | 169.51 | 48.35 | 17.35 | | |
| Ala$^1$ | 169.27 | 50.80 | 34.21 | — | |
| Ser$^2$ | 170.48 | 55.04 | 61.23 | | |
| Gly$^3$ | 168.90 | 43.44 | | — | |
| Trp$^4$ | | 54.28 | 27.62 | | 110.41, 123.28, 127.08, 111.28, 120.83, 136.00, 118.10, 118.22 |
| Val$^5$ | 171.20 | 56.73 | 31.50 | 17.76 19.02 | |
| Ala$^6$ | 170.14 | 53.47 | 32.79 | | |
| Abu$^7$ | | 57.83 | 43.95 | 19.96 | |
| Leu$^8$ | 171.45 | 51.01 | 41.66 | 24.03 | 22.38 22.62 |
| Abu$^9$ | 171.59 | 55.77 | 46.38 | 20.10 | |
| Ile$^{10}$ | 170.96 | 60.00 | 35.71 β-Me: 14.70 | 24.75 | 11.59 |
| Glu$^{11}$ | | 55.86 | 24.49 | 30.98 | 173.75 |
| Ala$^{12}$ | 170.78 | 55.47 | 35.26 | | |
| Gly$^{13}$ | 170.03 | 44.18 | | | |
| Abu$^{14}$ | 168.33 | 55.00 | | | |
| Val$^{15}$ | 170.63 | 60.03 | 30.02 | 19.15 18.564 | |
| Ile$^{16}$ | 170.66 | 59.64 | 35.69 β-Me: 15.53 | 24.55 | 10.62 |
| Ala$^{17}$ | 169.79 | 53.13 | 35.70 | | |
| Ala$^{18}$ | 171.52 | 48.89 | 15.34 | | |
| Ala$^{19}$ | | 47.16 | 51.53 | | |
| unassigned | 169.01 169.83 170.33 171.01 | | | | |

Amino acid analysis yields a further Ala additionally to the amino acids of actagardine [1 Ser, 2 Gly, 1 Trp, 2 Val, 1 Leu, 2 Ile, 1 Glu, 1 Ala, 1 lanthionine (Ala-S-Ala) and 3 β-methyllanthionine (Abu-S-Ala)].

It has furthermore been found that the compound according to the invention has strong antibacterial actions; Table 3 summarizes the minimum inhibitory concentrations (MIC) of Ala(0)-actagardine by way of example.

TABLE 3

In-vitro activity of Ala(0)-actagardine against gram-positive and anaerobic bacteria in the serial dilution test.

| MICROORGANISM | Ala(0)-actagardine MIC values (μg/ml) |
|---|---|
| Staph. aureus SG 511 | 6.25 |
| Staph. aureus 285 | 6.25 |
| Staph. aureus 503 | 3.13 |
| Staph. aureus FH 1982 | 12.5 |
| Staph. aureus 701 E | 12.5 |
| Staph. aureus 707 E | 12.5 |
| Staph. aureus 9 Tub. | 6.25 |
| Staph. aureus 8236 | 6.25 |
| S. epidermidis ZH2c | 6.25 |
| S. epidermidis 6098W | 12.5 |
| S. epidermidis 763 | 6.25 |
| S. epidermidis 5747IIW | 6.25 |
| S. epidermidis 291 | 12.5 |
| S. epidermidis 799 | 6.25 |
| E. faecium Md8B | 6.25 |
| E. faecium VR1 | 50 |
| E. faecium VR2 | 50 |
| S. pyogenes VR3 | 25 |
| S. pyogenes 308A | 6.25 |
| S. pyogenes 77A | 0.195 |
| Propionib. acnes 6919 | 1.0 |
| Propionib. acnes 6922 | 1.0 |
| Clostrid. tetani 9406 | 8.0 |
| Clostrid. perfringens 194 | 0.5 |

It is particularly worthy of note that the compound according to the invention has not only around twice as much antibacterial activity against gram-positive microorganisms as actagardine, but simultaneously no cross-resistance at all with conventional antibiotics, such as, for example, the β-lactams (penicillins, cephalosporins), aminoglycosides (streptomycin), macrolides (erythromycin), quinolones (ciprofloxacin), sulfonamides or glycopeptides (vancomycin) and others. Moreover to be emphasized is the strong inhibitory action on anaerobes, which can cause stubborn, indeed even life-threatening infectious diseases.

Ala(0)-actagardine is especially suitable for the therapy of such disorders.

The tolerability of Ala(0)-actagardine is good at the active concentration and above. Cytotoxic actions or other toxicities were not observed.

The present invention accordingly also relates to the use of the compounds according to the invention as pharmaceuticals, and the use of the compounds concerned for the production of pharmaceuticals for the treatment and/or prophylaxis of bacterial infections.

In addition, the present invention relates to pharmaceuticals which contain the compound according to the invention.

Said pharmaceutical is prepared by mixing at least one compound of the formula I with a physiological auxiliary and/or excipient and bringing it into a suitable administration form.

The pharmaceuticals according to the invention can be administered enterally (orally), parenterally (intramuscularly or intravenously), rectally or locally (topically). They can be administered in the form of solutions, powders (tablets, capsules including microcapsules), ointments (creams or gel), or suppositories. Possible auxiliaries for formulations of this type are the pharmaceutically customary liquid or solid fillers and extenders, solvents, emulsifiers, lubricants, flavor corrigents, colorants and/or buffer substances. As an expedient dose, 0.1–1000, preferably 0.2–100, mg/kg of body weight are administered. They are expediently administered in dose units which contain at least the efficacious daily amount of the compounds according to the invention, e.g. 30–3000, preferably 50–1000, mg.

The present invention is intended to be illustrated in greater detail by the following working examples and by the contents of the patent claims.

EXAMPLE 1

Preparation of a Mycelium Suspension of the Producer Strain 100 ml of nutrient solution (10 g of starch, 10 g of glycerol, 10 g of glucose, 2.5 g of Cornsteep, 5 g of peptone and 2 g of yeast extract in 1 l of mains water, pH before sterilization: 6.0) in a 500 ml sterile Erlenmeyer flask are inoculated with the strain and incubated on a rotating shaker for 72 hours at 28° C. and 140 rpm. 120 ml of culture fluid are then uniformly distributed in a sterile 500 ml Erlenmeyer flask containing the nutrient medium oatmeal infusion, 2.0 g/l, to which 15 g of agar/l have additionally been added for solidification, and decanted. The cultures are incubated at 28° C. for 10 to 14 days. The mycelium from a flask formed after this time is picked out, immediately reused or stored at −22° C. in 50% glycerol or in 10% dimethyl sulfoxide at −140° C.

EXAMPLE 2

Preparation of a Culture or a Preculture of the Producer Strain in an Erlenmeyer Flask A sterile 500 ml Erlenmeyer flask containing 100 ml of the nutrient solution described in Example 1 is inoculated with a culture grown in a slant tube or with a piece of agar and incubated at 140 rpm and 28° C. in the dark on a shaker. The maximum production of the compounds of the formula I is achieved after about 72 hours. A 72 hour-old submerse culture (inoculation amount about 5%) from the same nutrient solution suffices for inoculating 10 and 100 l fermenters.

EXAMPLE 3

Preparation of Ala(0)-Actagardine

A 10 l fermenter is operated under the following conditions:
Nutrient medium: 2% soybean flour 2% mannitol
Incubation time: 24 or 48 hours
Incubation temperature: 28° C.
Stirrer speed: 200 rpm
Aeration: 5 l of air/min.

Foam formation can be suppressed by repeated addition of a few drops of ethanolic polyol solution. The production maximum is achieved after 48 hours.

EXAMPLE 4

Isolation of the Antibiotic Ala(0)-Actagardine 27 l of the culture solution obtained according to Example 3 are centrifuged off and the clear culture filtrate is applied to a 3 l capacity column packed with the adsorption resin MCI Gel® CHP20P. Column dimensions: width×height: 11.3 cm×30 cm. The column is eluted with a solvent gradient of 5% isopropanol in water to 50% isopropanol and the column efflux is collected in fractions of 2 l each. The Ala(0)-actagardine-containing fractions, which are checked by HPLC analyses, are collected and concentrated in vacuo, and freeze-dried (4 g).

EXAMPLE 5

High-Pressure Liquid Chromatography (HPLC) of the Ala (0)-Actagardine

Column: Nucleosil® 100–5 $C_{18}$AB, 250/4.
Mobile Phase: 32% acetonitrile in 10 mM potassium phosphate buffer pH 7.
Flow rate: 1 ml per minute
Detection by UV absorption at 210 nm.

For Ala(0)-actagardine, the retention time of 16 min 50 seconds was found, for actagardine itself 11 min and 20 seconds.

EXAMPLE 6

Concentration of the Ala(0)-Actagardine 3 g of the product obtained according to Example 4 are applied to a 3 liter capacity column packed with Fractogel® TSK HW-40 s (width×height=10 cm×50 cm). The eluent, 50% methanol in water, is pumped through the column at a flow rate of 50 ml per minute and the column efflux is collected in fractions (65 ml). The antibiotic Ala(0)-actagardine, 140 mg, is found mainly in fractions 24 to 28.

EXAMPLE 7

Final Purification of the Ala(0)-Actagardine

The enriched antibiotic Ala(0)-actagardine (280 mg), obtained according to Example 6, is applied to a Nucleosil® 12$C_{18}$AB-HPLC column (width×height=3.2 cm×25 cm) in the gradient procedure using 5% to 30% acetonitrile and 0.05% trifluoroacetic acid. The fractions investigated by analytical HPLC (see Example 5) are correspondingly combined, concentrated in vacuo and freeze-dried. They afford 185 mg of Ala(0)-actagardine in 98% purity.

Molecular weight of the Ala(0)-actagardine determined by ESI+ mass spectrometry: $M+H^+=1962.6$.

EXAMPLE 8

Obtainment of Lys(0)-Actagardine 94.5 mg (0.05 mmol) of actagardine are dissolved in 10 ml of anhydrous dimethylformamide (DMF) and 22 mg (0.05 mmol) of di-Boc-lysine O-N-hydroxysuccinimide and also 100 µl of triethylamine (TEA) are added and the mixture is allowed to stand at room temperature. The course of the reaction is monitored analytically by means of HPLC (see Example 5). After 96 hours, the reaction is discontinued by stripping off the DMF and the TEA in a high vacuum and the reaction product is purified by preparative HPLC in the gradient procedure using 25 to 50% acetonitrile in 0.05% strength trifluoroacetic acid (TFA). The column dimensions are height×width 25 mm 250 mm; support: Select B®. After freeze-drying of the reaction product-containing fractions, 33 mg (0.015 mmol) of di-Boc-Lys(0)-actagardine are obtained.

The Boc protective groups are completely removed with 60% strength TFA. To do this, 25 mg (0.011 mmol) of the protected derivative are dissolved in 5 ml of 60% strength TFA at room temperature. After

TABLE 6

| Incubation time: 18 h | Ala—Acta | Ile—Acta | Boc—Phe—Acta | Lys—Acta | Boc—Lys—Acta |
|---|---|---|---|---|---|
| S. aureus 011HT3 | 20 | 2.5 | 5 | 10 | 10 |
| S. aureus 011HT3 + 10% serum | 20 | 2.5 | 10 | 10 | 20 |
| S. aureus 011HT3 + 50% serum | 40 | 5 | 40 | 10 | 40 |
| S. aureus 011HT18 | >40 | >40 | >40 | >40 | >40 |
| S. epidermidis 012GO20 | >40 | >40 | >40 | >40 | >40 |
| S. aureus 011HT1 | 1.1 | 1.2 | 10 | 0.6 | 10 |
| S. aureus 011DU5 | 40 | 10 | 40 | 10 | 40 |
| S. aureus 011CB20 | >40 | 40 | >40 | >40 | — |
| S. aureus 0121O64 | >40 | >40 | >40 | >40 | >40 |
| S. epidermidis 012GO42 | >40 | >40 | >40 | >40 | >40 |
| Staph. coag. negative 012HT5 | >40 | >40 | >40 | >40 | >40 |
| S. pyogenes 02A1SJ1 | <=0.04 | <=0.04 | 0.08 | <=0.04 | 0.08 |
| S. pyogenes 02A1UC1 | <=0.04 | <=0.04 | <=0.04 | <=0.04 | <=0.04 |
| S. pyogenes 02A1FI6 | <=0.04 | <=0.04 | <=0.04 | <=0.04 | <=0.04 |
| Strepto gr. G 02G0CB2 | 20 | 10 | 2.5 | 5 | 2.5 |
| S. pneumoniae 030BI2 | 2.5 | 1.2 | 1.2 | 2.5 | 1.2 |
| S. milleri 02milGR12 | 40 | >40 | 40 | 40 | 5 |
| S. mitis 02mitGR16 | 20 | 10 | 20 | 10 | 5 |
| E. faecalis 02D2HM9 | >40 | 40 | 40 | >40 | >40 |
| E. faecalis 02D2UC5 | 20 | 40 | 40 | 40 | 40 |
| E. faecalis 02D2DU18 | 5 | 5 | 10 | 5 | 10 |
| E. faecalis 02D2HT10 | >40 | >40 | >40 | >40 | >40 |

90 minutes, removal is complete. The free lysyl-actagardine is purified using the same gradient, as described above, on a preparative HPLC column (10 mm×250 mm, LiChrospher®). The freeze-drying of the purified material affords 14 mg (0.007 mmol) of Lys(0)-actagardine. The molecular weight of the final product is checked by mass spectrometry. It is (M+H)$^+$: 2019, corresponding to the empirical formula $C_{87}H_{136}O_{25}N_{22}S_4$.

EXAMPLE 9
The Preparation of Ile(0)-Actagardine 189 mg (0.1 mmol) of actagardine are reacted with 33 mg (0.1 mmol) of Boc-Ile-O-N-hydroxysuccinimide ester as described in Example 8. 210 mg of Boc-Ile(0)-actagardine are obtained.

Removal of the Boc protective group and final purification afford 84 mg (0.042 mmol) of Ile(0)-actagardine.

The molecular weight determined by mass spectrometry is (M+H)$^+$: 2004, corresponding to the empirical formula $C_{87}H_{135}O_{25}N_{21}S_4$.

EXAMPLE 10
The Preparation of N-α-Aminobutyryl-Actagardine [Abu (0)-Actagardine]

94.5 mg (0.05 mmol) of actagardine are reacted with 16.3 mg (0.05 mmol) of para-nitrophenyl N-Boc-α-aminobutyrate as described in Example 8. After 9 days, 54 mg of N-Boc-Abu(0)-actagardine result and, after removal of the protective group, 19 mg (0.01 mmol) of N-α-aminobutyryl-actagardine.

Molecular peak (M+H)$^+$: 1976, corresponding to the empirical formula $C_{85}H_{131}O_{25}N_{21}S_4$.

EXAMPLE 11
The Preparation of Gln(0)-Actagardine 94.5 mg (0.05 mmol) of actagardine are reacted with 16.4 mg (0.05 mmol) of Boc-glutamine paranitrophenyl ester as described in Example 8. After removing the protective group, 38 mg (0.019 mmol) of Gln(0)-actagardine are obtained.

Molecular peak (M+H)$^+$: 2019, corresponding to the empirical formula $C_{86}H_{132}O_{26}N_{22}S_4$.

EXAMPLE 12
The Preparation of Phe(0)-Actagardine 94.5 mg (0.05 mmol) of actagardine are reacted with 15.6 mg (0.05 mmol) of Boc-Phe-O-N-hydroxysuccinimide ester as described in Example 8. After removal of the protective group, 26 mg (0.013 mmol) of Phe(0)-actagardine are obtained.

Molecular peak (M+H)$^+$: 2038, corresponding to the empirical formula $C_{90}H_{133}O_{25}N_{21}S_4$.

EXAMPLE 13
The Preparation of Phe-Ala(0)-Actagardine 94.5 mg (0.05 mmol) of actagardine are reacted with 21.7 mg (0.05 mmol) of Boc-Phe-Ala-O-N-hydroxysuccinimide ester for 3 hours as described in Example 8. After removing the protective group, 37 mg (0.018 mmol) of Phe-Ala(0)-actagardine are obtained.

Molecular peak (M+H)$^+$: 2109, corresponding to the empirical formula $C_{93}H_{138}O_{26}N_{22}S_4$.

EXAMPLE 14
The Preparation of D-Ala(0)-Actagardine 94.5 mg (0.05 mmol) of actagardine are reacted with 14.5 mg (0.05 mmol) of Boc-D-Ala-O-N-hydroxysuccinimide ester for 24 hours as described in Example 8. After removing the protective group, 47 mg (0.024 mmol) of D-Ala(0)-actagardine are obtained.

Molecular peak (M+H)$^+$: 1961, corresponding to the empirical formula $C_{84}H_{129}O_{25}N_{21}S_4$.

Tables 4 to 6 show the in-vitro antibacterial activity (MIC values[μg/ml]) of the actagardine (Acta) and of the compounds according to the invention.

TABLE 4

| Incubation time: 24 h | Acta | Ala—Acta | Ile—Acta | Gln—Acta | Phe—Acta | Phe—Ala—Acta | Lys—Acta | Abu—Acta |
|---|---|---|---|---|---|---|---|---|
| *S. aureus* SG511 | 20 | 5 | 1.2 | 20 | 0.6 | 5 | 1.2 | 1.2 |
| *S. aureus* SG511 + 10% serum | 40 | 20 | 2.5 | 40 | 5 | 10 | 2.5 | 10 |
| *S. aureus* Exp54146 | >40 | 40 | 2.5 | >40 | 5 | 20 | 10 | 20 |
| *S. pyogenes* A561 | >40 | <=0.04 | <=0.04 | 5 | >40 | >40 | <=0.04 | >40 |
| *E. faeccium* M78L | 10 | 5 | 5 | 10 | >40 | 10 | 5 | >40 |
| *E. Coli* | >40 | >40 | >40 | >40 | >40 | >40 | >40 | >40 |

TABLE 5

| Incubation time: 24 h | Acta | Boc—Ala—Acta | Boc—Ile—Acta | Boc—Gln—Acta | Boc—Phe—Acta | Boc—Phe—Ala—Acta |
|---|---|---|---|---|---|---|
| *S. aureus* SG511 | 20 | 10 | 20 | 40 | 1.2 | 5 |
| *S. aureus* SG511 + 10% serum | 40 | 40 | 40 | >40 | 10 | 10 |
| *S. aureus* Exp54146 | >40 | 40 | >40 | >40 | 5 | 10 |
| *E. faeccium* M78L | >40 | 20 | >40 | 40 | 5 | >40 |
| *E. Coli* | >40 | >40 | >40 | >40 | >40 | >40 |

| Incubation time: 24 h | Boc—Lys—Acta | Boc—Abu—Acta |
|---|---|---|
| *S. aureus* SG511 | 2.5 | 5 |
| *S. aureus* SG511 + 10% serum | 10 | 10 |
| *S. aureus* Exp54146 | 10 | >40 |
| *S. pyogenes* A561 | <=0.04 | >40 |
| *E. faeccium* M78L | 10 | >40 |
| *E. Coli* | >40 | >40 |

We claim:
1. A compound of the formula I

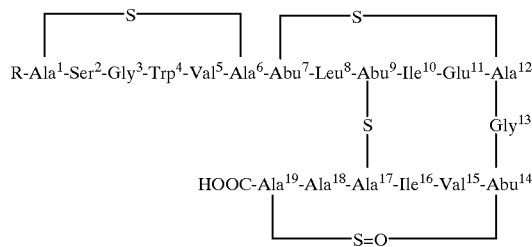

where R is a radical of an amino acid, or its physiologically tolerable salts.

2. A compound of the formula I as claimed in claim 1 in which R is the radical of a natural amino acid.

3. A compound of the formula I as claimed in claim 2 in which the amino acid is Ala, Ile, Lys, Phe or Val.

4. A compound of the formula I as claimed in claim 3 in which the amino acid is Ala.

5. A compound of the formula I as claimed in claim 1 in which the amine nitrogen of the amino acid carries a removable protective group.

6. A process for the preparation of a compound as claimed in claim 1, which comprises reacting actagardine with an amino acid and optionally converting it into its pharmacologically tolerable salts.

7. A process for the preparation of a compound as claimed in claim 1, which comprises fermenting the microorganism *Actinoplanes liguriae*, DSM 11797 or *Actinoplanes garbadiensis*, DSM 11796 or one of their variants or mutants in a culture medium, isolating a compound of the formula I and optionally converting it into its pharmacologically tolerable salts.

8. A process as claimed in claim 7, wherein *Actinoplanes liguriae*, DSM 11797 or *Actinoplanes garbadiensis*, DSM 11796 or their mutants and/or variants are fermented under aerobic conditions in culture media containing a carbon and nitrogen source and also the customary inorganic salts and trace elements.

9. A process as claimed in claim 8, wherein the fermentation is carried out in a nutrient medium which, as carbon source, contains 0.5 to 5% of mannitol and 0.5 to 5% of soybean flour.

10. A process as claimed in claim 8, wherein the fermentation is carried out under aerobic conditions at a temperature between 20 and 35° C. and at a pH between 4 and 10.

11. A compound as claimed in claim 1 for use as a pharmaceutical.

12. A process for the production of a pharmaceutical which comprises bringing at least one compound as claimed in claim 1 into a suitable administration form with a physiological auxiliary and/or excipient.

13. A method for the treatment and prophylaxis of bacterial infectious diseases comprising administration of a compound as claimed in claim 1 together with one or more physiologically acceptable excipients to a host in need thereof.

* * * * *